US012714487B2

(12) United States Patent
Selig et al.

(10) Patent No.: US 12,714,487 B2
(45) Date of Patent: Aug. 25, 2026

(54) ACTIVE ELECTROSURGICAL INSTRUMENT

(71) Applicant: Erbe Elektromedizin GmbH, Tuebingen (DE)

(72) Inventors: Peter Selig, Nehren (DE); Konstantin Dornhof, Horb am Neckar (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 1057 days.

(21) Appl. No.: 17/707,592

(22) Filed: Mar. 29, 2022

(65) Prior Publication Data

US 2022/0313345 A1 Oct. 6, 2022

(30) Foreign Application Priority Data

Mar. 31, 2021 (EP) .................................... 21166320

(51) Int. Cl.
*A61B 18/12* (2006.01)
*A61B 18/00* (2006.01)
(Continued)

(52) U.S. Cl.
CPC .......... *A61B 18/1206* (2013.01); *A61B 18/10* (2013.01); *A61B 18/14* (2013.01);
(Continued)

(58) Field of Classification Search
None
See application file for complete search history.

(56) References Cited

U.S. PATENT DOCUMENTS 3,658,067 A 4/1972 Bross
3,885,569 A * 5/1975 Judson .................. A61B 18/12 606/37

(Continued)

FOREIGN PATENT DOCUMENTS

CA 2286835 A1 10/1998
CN 101031249 A 9/2007

(Continued)

OTHER PUBLICATIONS

Extended European Search Report dated Sep. 24, 2021, in corresponding European Application No. 21166230.8, with machine English translation (14 pages).

(Continued)

*Primary Examiner* — Sean W Collins
*Assistant Examiner* — Nora W Rhodes
(74) *Attorney, Agent, or Firm* — Fitch, Even, Tabin & Flannery LLP

(57) ABSTRACT

The electrosurgical instrument (11) according to the invention comprises at least one electrode (15, 16) for electrically acting on biological tissue. The electrode is coupled with a radio frequency generator (20) that is arranged in direct proximity of electrode (15) and/or (16). The radio frequency generator oscillates in a self-controlled manner with a frequency between 100 kHz and 10 MHz and is preferably supplied by a constant or timely varying direct voltage. The instrument (11) is thus connected via a line supplying a low frequency voltage or direct voltage with a supplying source, e.g. an apparatus (19).

15 Claims, 4 Drawing Sheets

(51) Int. Cl.
*A61B 18/10* (2006.01)
*A61B 18/14* (2006.01)

(52) U.S. Cl.
CPC ............... *A61B 2018/00732* (2013.01); *A61B 2018/00767* (2013.01); *A61B 2018/00827* (2013.01); *A61B 2018/00845* (2013.01); *A61B 2018/00892* (2013.01)

(56) References Cited

U.S. PATENT DOCUMENTS

| | | | | |
|---|---|---|---|---|
| 4,038,984 | A | 8/1977 | Sittner | |
| 5,825,256 | A | 10/1998 | Tchamov et al. | |
| 5,896,070 | A | 4/1999 | Tchamov et al. | |
| 5,952,862 | A | 9/1999 | Tchamov et al. | |
| 5,990,718 | A | 11/1999 | Tchamov et al. | |
| 6,039,734 | A | 3/2000 | Goble | |
| 6,562,037 | B2 | 5/2003 | Paton et al. | |
| 6,929,641 | B2 | 8/2005 | Goble et al. | |
| 7,896,875 | B2 | 3/2011 | Heim et al. | |
| 9,155,585 | B2 | 10/2015 | Bales, Jr. et al. | |
| 2010/0137854 | A1 | 6/2010 | Hosier | |
| 2011/0112530 | A1 | 5/2011 | Keller | |
| 2011/0245826 | A1 | 10/2011 | Woloszko et al. | |
| 2014/0114327 | A1* | 4/2014 | Boudreaux ............ | A61B 34/25 606/130 |
| 2014/0148803 | A1 | 5/2014 | Taylor | |
| 2015/0305798 | A1 | 10/2015 | Garito et al. | |
| 2015/0313628 | A1 | 11/2015 | Allen, IV | |
| 2016/0270841 | A1 | 9/2016 | Strobl et al. | |
| 2017/0079710 | A1 | 3/2017 | Deville et al. | |
| 2017/0202607 | A1 | 7/2017 | Shelton, IV et al. | |
| 2017/0238987 | A1 | 8/2017 | Fregoso | |

FOREIGN PATENT DOCUMENTS

| | | | |
|---|---|---|---|
| CN | 101500502 | B | 1/2013 |
| CN | 105742151 | A | 7/2016 |
| CN | 112386328 | A | 2/2021 |
| DE | 2023140 | A1 | 11/1970 |
| DE | 2901153 | A1 | 7/1979 |
| DE | 2910196 | B1 | 9/1980 |
| DE | 19780481 | T1 | 8/1998 |
| DE | 19780470 | T1 | 10/1998 |
| DE | 19719440 | C2 | 1/2002 |
| DE | 19719441 | C2 | 5/2002 |
| DE | 202008001365 | U1 | 5/2008 |
| DE | 602004009293 | T2 | 7/2008 |
| EP | 1599146 | B1 | 10/2007 |
| EP | 2572669 | B1 | 4/2017 |
| EP | 2572668 | B1 | 5/2018 |
| JP | S 50-074194 | U | 11/1948 |
| JP | S 61-222441 | A | 10/1986 |
| JP | 2002502660 | A | 1/2002 |
| JP | 2011-161230 | A | 8/2011 |
| JP | 2012501696 | A | 1/2012 |
| JP | 2016-500921 | A | 1/2016 |
| JP | 2016-502416 | A | 1/2016 |
| JP | 2016-195791 | A | 11/2016 |
| RU | 2572748 | C2 | 1/2016 |
| WO | 2007/100697 | A2 | 9/2007 |

OTHER PUBLICATIONS

Japanese Patent Office; Japan Notice of Reasons for Refusal in corresponding Japanese Patent Application No. 2022-038979, dated Jun. 17, 2025; 15 pages.

National Intellectual Property Administration, P. R. China, Chinese Office Action and Search Report in corresponding Chinese Patent Application No. 202210325368.X dated Jul. 17, 2024; 21 pages.

Federal Service for Intellectual Property of the Russian Federation; Russian Search Report in corresponding Russian Application No. 2022107943/14 (016562), completed Feb. 20, 2025; 4 pages.

Federal Service for Intellectual Property of the Russian Federation; Russian Office Action in corresponding Russian Application No. 2022107943/14 (016562), dated Feb. 20, 2025, 20 pages.

Intellectual Property India; Examination Report in corresponding Indian Patent Application No. 202234015512, dated Feb. 9, 2026; 7 pages.

The National Institute of Industrial Property (INPI); Office Action with partial translation in corresponding Brazilian Patent Application No. 102022004999-8, dated Mar. 10, 2026, 5 pages.

Japan Patent Office; Notification of Grant in corresponding Japanese Patent Application No. 2022-038979, dated Sep. 16, 2025.

* cited by examiner 19
18
15
17
16
20
23
28
26
27
25
24
11

20
32
36'
S
15
UHF
16
36
34
33
35
$T_4$
$Z_2$
$T_2$
$T_3$
$Z_1$
$T_1$
150V
31
22
30
G
0V

ACTIVE ELECTROSURGICAL INSTRUMENT

RELATED APPLICATION(S)

This application claims the benefit of European Patent Application No. 21166320.8, filed Mar. 31, 2021, the contents of which are incorporated herein by reference as if fully rewritten herein.

TECHNICAL FIELD

The invention refers to an electrosurgical instrument with an energized electrode for carrying out electrosurgical interventions on a human or animal patient.

BACKGROUND

Electrosurgical instruments, probes or the like typically require an electrosurgical generator for supplying the instrument with radio frequency alternating current. For this purpose DE 60 2004 009 293 T2 discloses an electrosurgical system having a generator to which an instrument can be connected that is to be supplied with radio frequency current from the generator. In an embodiment the instrument comprises coagulation electrodes as well as a cutting electrode that are alternatingly supplied in fast sequence in order to concurrently operate with them. A respective electronic selector switch is provided for this purpose in the instrument itself.

U.S. Pat. No. 7,896,875 B2 and U.S. 2011/0112530 describe an RF instrument respectively, the external generator of which is supplied by means of a battery. U.S. Pat. No. 9,155,585 B2 further describes a battery-operated electromedical generator with externally controlled transistors. An instrument with installed battery and installed generator emerges from US 2015/0305798.

Further the use of microwaves for medical treatment is known from EP 2 572 668 B1 as well as EP 2 572 669 B1. Respective instruments comprise a microwave antenna arranged on a distal end of a longitudinal shaft that is supplied from a microwave amplifier arranged in the instrument. The instrument is connected via a cable with a microwave signal generator, the signal of which is transmitted to the microwave amplifier. In a modified embodiment the microwave signal generator is arranged in the handle of the instrument. A selector switch allows changeover between a microwave signal of an external signal generator and the microwave signal of the internal signal generator.

An instrument with installed generator is also known from U.S. Pat. No. 6,039,734 that comprises a monopolar electrode for treatment of a patient and closes the current circuit via the treating person in a capacitive manner. The operation frequency is higher than 5 MHz. Finally further prior art emerges from U.S. 2017/238987 A1, U.S. 2017/202607 A1, U.S. 2017/079710 A1, U.S. 2016/0270841 A1, U.S. 2014/148803 A1, DE 20 2008 001 365 U1 and CA 2 286 835 A1.

While microwave generators heat and influence tissue by radiation of microwaves, radio frequency operated surgical instruments operate with remarkably lower frequencies. The frequency of current supplied by such instruments for operation is typically around some 100 kHz. Such instruments operate with a radio frequency current flow through the tissue and always require two electrodes in abutment with the tissue for this purpose. The instruments serve for carrying out different measures that are directly linked to the direct current flow through the biological tissue, such as cutting, coagulating, fusioning, ablating or the like. The desired surgical effects can be accurately influenced by means of the shape and use of respective electrodes. Thereby different RF voltages and RF currents are used just like different modulation forms, e.g. non-modulated RF (CW—"Continuous Wave"), amplitude modulated, e.g. pulsed with or without pulse width modulation and so and so forth. Moreover, current/voltage-dependencies can be defined by means of respective generator output characteristic curves that are beneficial for surgery success.

However, for the operation of such a surgical instrument typically an external surgical generator is required that has to provide the required modes and from which the radio frequency power is transmitted via a cable to the instrument. The modes distinguish, for example, by voltage, current, power, modulation and much more.

DE 29 01 153 A1, U.S. 2010/0137854 A1, U.S. 2011/0245826 A1 and EP 1 599 146 B1 disclose generators with externally controlled switches for exciting of one or more resonant circuits.

Besides medical applications, e.g. in the telecommunication technology, self-oscillating generators are used as for example known from DE 197 80 481 T1, DE 197 80 470 T1, DE 197 19 440 C2 or DE 197 19 441 C2. These generators are configured as voltage-controlled push-pull-oscillators for ultra/super high frequency range of 1-20 GHz. Thereby it shall be operated with a very low operating voltage of, for example, only 4.5 V. The circuits are suitable for the milliwatt range. On the contrary, in the field of electrosurgery it is operated with remarkably higher voltages, higher powers and substantially higher voltages. Thereby the danger of voltage overload of individual components exists.

It is one object of the invention to provide an improved instrument.

SUMMARY

This object is solved by means of an instrument and in addition by means of an arrangement as described herein:

The electrosurgical instrument according to the invention comprises two electrodes for acting on biological tissue. If only one electrode is provided for acting on the tissue, at least one second electrode is provided that is to be attached on the patient as neutral electrode spaced apart from the surgery location. Therefore the instrument can be configured as monopolar instrument that has an electrode for carrying out surgical interventions as well as a neutral electrode to be attached on the patient (or a connection for a neutral electrode) in order to close the electric circuit for the treatment current. A radio frequency generator is arranged on or in the instrument that is configured as self-oscillating oscillator. A radio frequency generator provides the electrical power required for the surgical intervention.

On the input or primary side the radio frequency generator is connected or connectable to a direct voltage source or a low frequency alternating voltage source (e.g. 50 Hz or 60 Hz). On the output or secondary side the radio frequency generator is connected with the electrodes. The electrodes can be two active electrodes provided at the distal end of the instrument or one single active electrode and a neutral electrode that are connected to the radio frequency output of radio frequency generator. The radio frequency generator oscillates with a frequency between 100 kHz and 10 MHz, typically multiple 100 kHz, e.g. 350 kHz, 500 kHz or with another frequency inside the indicated range (e.g. 4 or 5 MHz). Due to the radio frequency generation in the electrosurgical instrument, the requirement of transmitting radio frequency voltages and currents over longer lines (multiple meters length) is omitted, such that particularly also radiation problems and problems with electro-magnetical compatibility are omitted.

It is possible to let the radio frequency generator oscillate with one single frequency such that the current flowing to the electrodes comprises a narrow spectrum. However, it is also possible to modulate the current output from the radio frequency generator in a manner such that a wide frequency spectrum is created that usually can result in a disturbance of adjacent electrical devices during transmission via electrical lines due to the antenna effect of radio frequency radiation related therewith. This occurs particularly in case of a pulse width modulation with very short impulses with very high voltage (multiple thousand volts). Due to the direct proximity between the radio frequency generator and the electrodes, radiation problems can be largely avoided, also in case of broadband and powerful signals. It is sufficient to supply a direct voltage or low frequency alternating voltage to the electrosurgical instrument, such that the supply line emits low or no electromagnetic interference radiation. The cable for current supply of the instrument can be a non-shielded line with two or multiple cores (conductors). Such cables can be substantially more flexible than shielded cables.

The radio frequency generator is preferably configured as push-pull-oscillator, particularly as free-running push-pull-oscillator. “Free-running” means that the oscillation of the push-pull-oscillator is maintained in the push-pull-oscillator by positive feedback. It is possible to build such push-pull-oscillators with particularly high efficiency and very low power loss. This applies particularly, if the push-pull-oscillator comprises a push-pull-flip-flop with two alternatingly switching transistors to the output electrodes of which one voltage amplifier is connected respectively. The output electrode of the transistors are their collectors in case of using PNP-transistors. If field effect transistors are used, the output electrodes are their drain electrodes. The downstream voltage amplifiers are, for example, bipolar transistors in common base circuit or field effect transistors in common gate circuit.

Basically NPN-transistors, IGBTs, N- or P-MOSFETs of depletion type or enhancement type, junction-gate field effect transistors, gallium nitride transistors (GaN) or the like can be used as transistors. Due to self-control of the radio frequency generator, the transistors of the push-pull-flip-flop do not switch in overlapping manner and switch respectively in idle condition without applied voltage and/or current flow, such that power losses at the transistors are minimum. The connected voltage amplifiers keep the high voltages of typically above 100 V provided at the radio frequency generator output away from the flip-flop. The flip-flop can operate with only 10 or 20 Volt, i.e. with low voltage.

The radio frequency generator preferably comprises a parallel resonant circuit consisting of at least one inductor and at least one capacitor connected in parallel with one another. The parallel resonant circuit preferably forms the frequency determining component of the radio frequency generator, wherein the feedback to the push-pull-flip-flop is achieved by means of the currents flowing through the two voltage amplifiers.

The decoupling of electrical radio frequency energy out of the parallel resonant circuit is preferably carried out by means of a decoupling inductor that is in transformer coupling with the inductor of the parallel resonant circuit. The transformer configured in this way can be configured for potential isolation between the patient circuit and the radio frequency generator complying with the standard. Preferably both ends of the decoupling inductor are directly connected with the electrodes that get into contact with the biological tissue. Particularly preferably no additional components and particularly no current or voltage measurement sensors are arranged between the inductor and the electrodes. In doing so, the load of the radio frequency output of the radio frequency generator with stray capacitances and the creation of capacitive leak currents is minimized. Due to omission of any current and voltage, sensors on the RF side, not only capacitive leak currents are minimized, but also particular simple circuit configuration is achieved. It shows that a measurement device for detection of voltage and/or current and/or power and/or frequency can be arranged on the direct voltage side. Accordingly, a respective measurement device can be located in the instrument or also in a supplying apparatus. The measurement device can create a signal that serves for open loop or closed loop control of the operation of the radio frequency generator. For example, the power, the current, the voltage or another electrical parameter output to the biological tissue can be regulated. The condition of the tissue to which the current is applied can be determined based on the measured current or based on the measured frequency and the instrument can be controlled accordingly. For example, the radio frequency generator can be switched off, if a tissue fusion process has been completed. The completion can be detected based on the current, if it falls below a threshold. Alternatively or additionally, the radio frequency generator can be switched off in a time-controlled manner.

It is further possible to connect the supply voltage input of the radio frequency generator with a voltage modulation device that can be located in the instrument or in a supplying apparatus. The voltage modulation device can be connected with the measurement device in order to provide an RF power with a desired current/voltage characteristic or a desired modulation.

The direct voltage source can thus output a defined non-varying direct voltage, an adjustable direct voltage that does not vary over time or a direct voltage that varies depending on time or load. Because losses in a (push-pull-) oscillator are low and are substantially constant over the load range, the voltage and the power of the primary side of the radio frequency oscillator (direct voltage side) indicate the voltages, currents and powers on the radio frequency side (secondary side) with sufficient accuracy for realization of simple effects, such as bipolar coagulation, a closed loop control of the radio frequency generator, particularly its power or its voltage, can also be completely avoided. For example, for this purpose the internal resistance of the radio frequency generator can be adapted to the respective surgical application. Such an adaptation can be carried out, for example, by dimensioning of the generator or its components or the like or by adjustment measures of the generator. Particularly, such an adaptation can be carried out by suitable definition of the winding ratio of the resonant circuit inductor relative to the decoupling inductor.

Due to the concept according to the invention, it becomes possible to operate with frequencies of up to 5 MHz at concurrently extremely low power input due to a respective modulation of the RF voltage. For example, the power input can be made very low by a pulse/pause modulation of the RF signal with a very low pulse/pause ratio. Thereby a possible plasma created at the electrode can be kept cool, such that its chemical effect is medically effective and the thermal surgical effect is pushed into the background or disappears.

BRIEF DESCRIPTION OF THE DRAWINGS

Details of advantageous embodiments of the invention are derived from the claims as well as the figures of the drawing and the respective description. The drawing shows:

DETAILED DESCRIPTION

Figures 1, 2, 3:
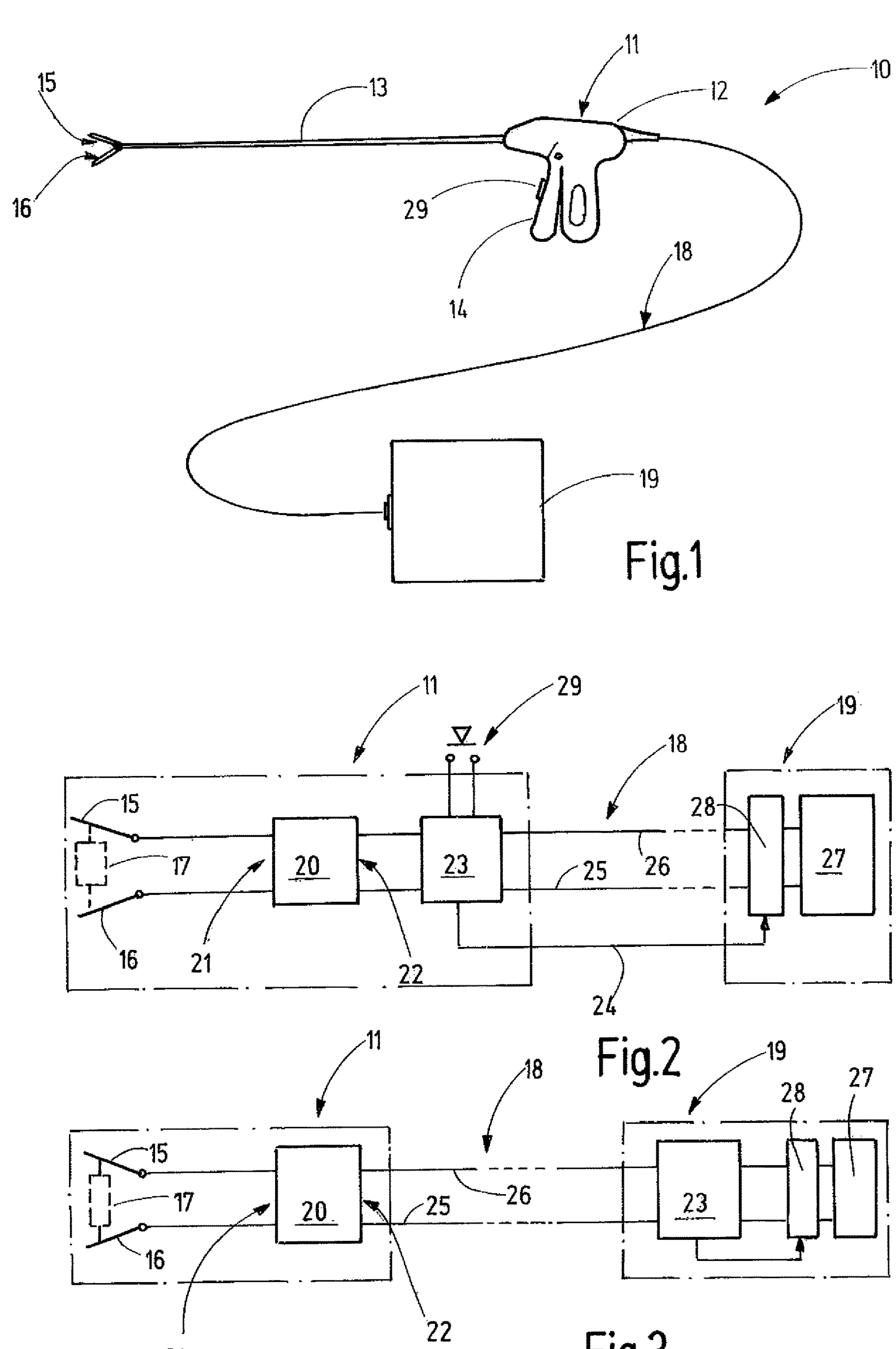
FIG. 1 an arrangement having an instrument and a supplying apparatus in a descriptive illustration, FIG. 2 the arrangement of FIG. 1 in a block diagram illustration, FIG. 3 a modified embodiment of the arrangement of FIG. 1 in block diagram illustration, FIG. 4 a further modified embodiment of the arrangement of FIG. 1 in block diagram illustration, FIG. 5 the circuit principle of the arrangement of FIGS. 1 to 4 for clarification of the circuit concept of the radio frequency generator, FIG. 6 a detailed illustration of the circuit of the arrangement according to FIGS. 1 to 4, FIG. 7 a further modified embodiment of the arrangement of FIG. 1 in a block diagram illustration, FIG. 8 a further modified embodiment of the arrangement of FIG. 1 in block diagram illustration.
Figures 4, 5:
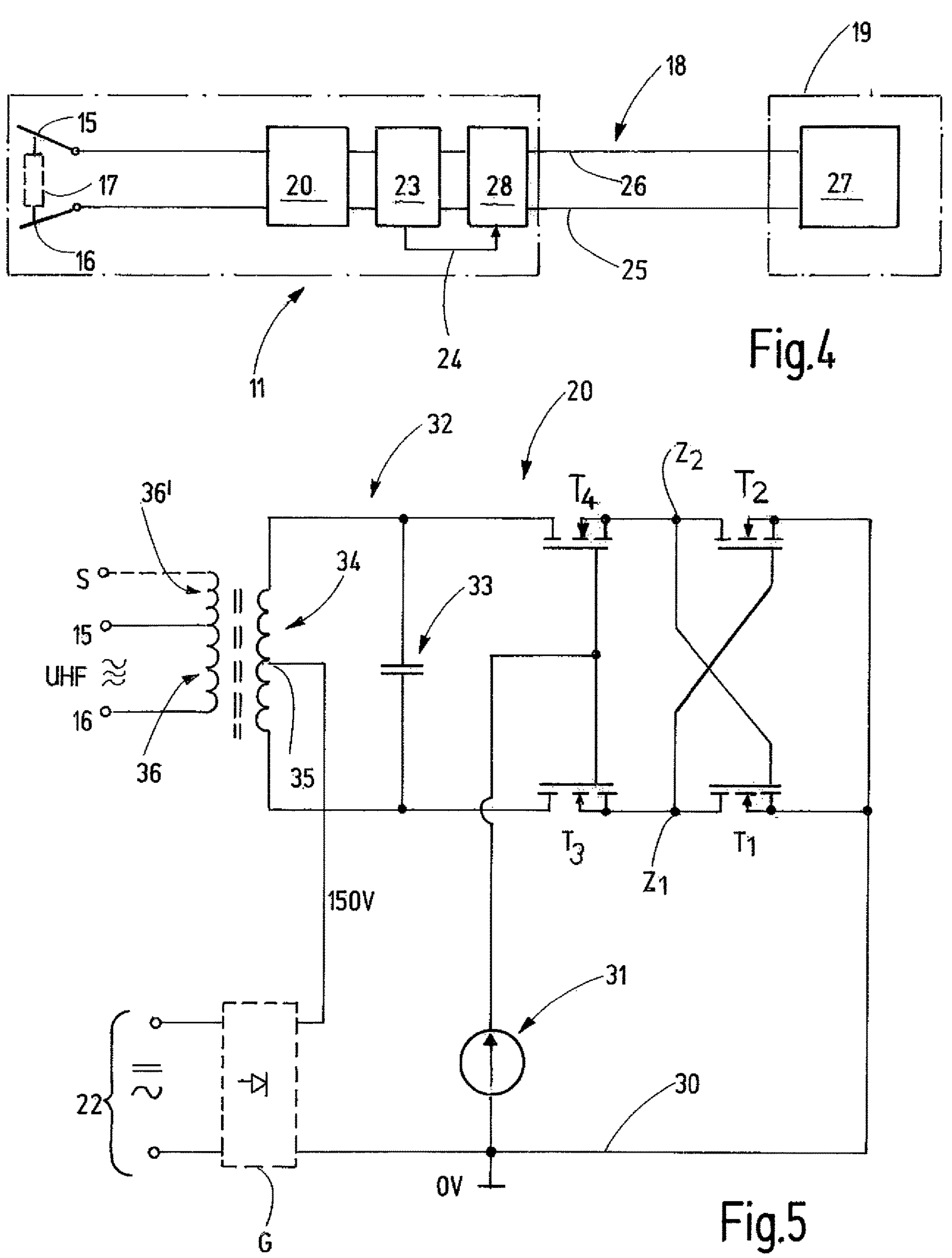

An arrangement 10 for surgical influence on a patient is illustrated in FIG. 1. An instrument 11 that is illustrated as laparoscopic bipolar instrument for sake of clarity here is part of the arrangement 10. Starting from its handle configured as housing, a shank 13 extends at the distal end of which a tool with, for example, two jaws is supported that can be opened and closed in the type of forceps by actuation of a hand lever 14. For example, on the sides of the jaws facing one another electrodes 15, 16 are arranged that are suitable to directly apply a current on tissue 17 located there between and compacted due to actuation of the hand lever 14, i.e. a current flow is allowed between the electrodes 15, 16 through tissue 17. The tissue 17 is illustrated in FIGS. 2, 3 and 4 respectively by a dashed illustrated ohmic resistor.

Figures 7, 8:
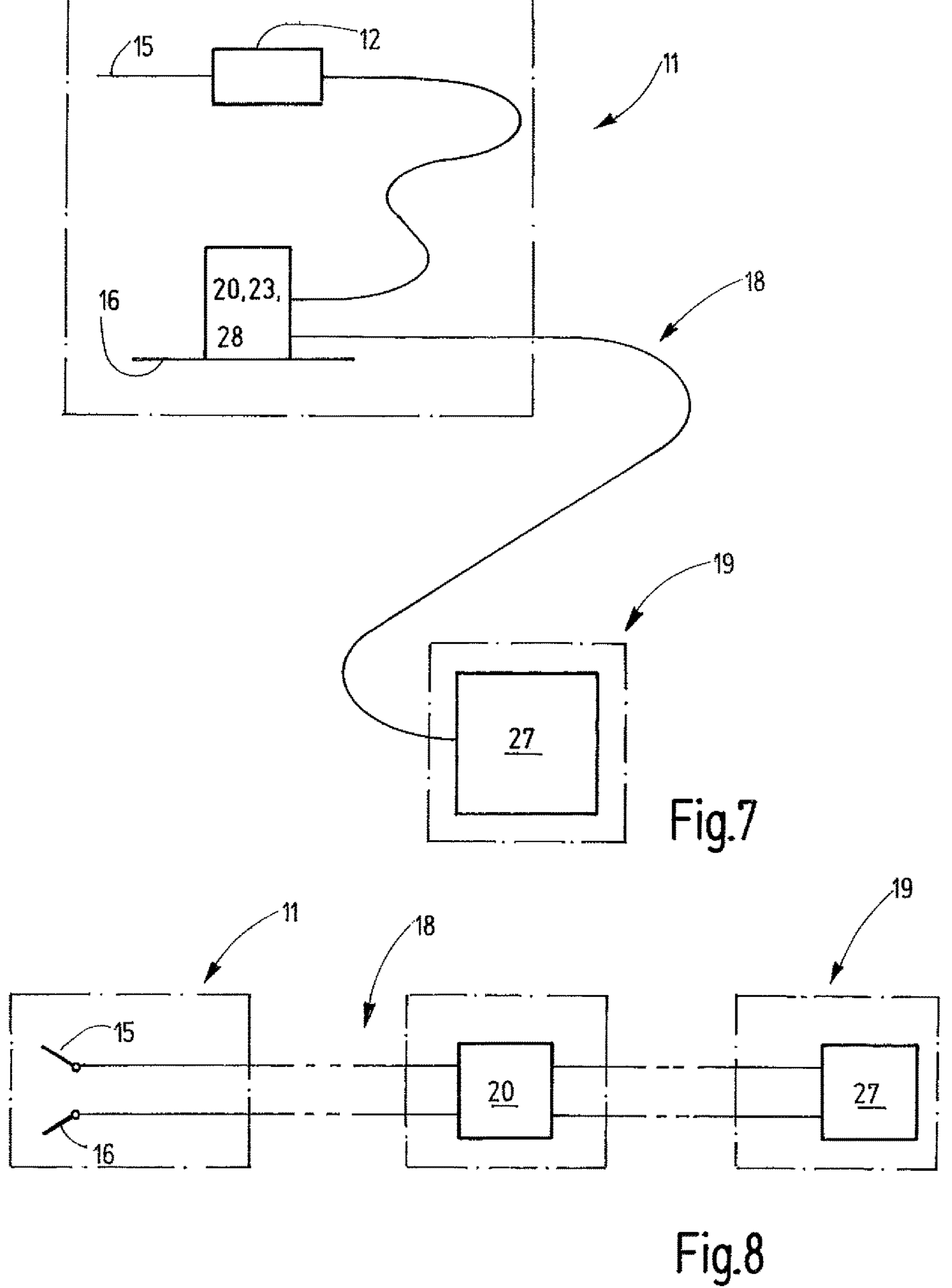

The instrument 11 can basically also be configured in another not illustrated manner. It is particularly possible to configure it as open surgical instrument, e.g. as electrosurgical forceps instrument, or to provide one or more additional electrodes in addition to the electrodes 15, 16. For example, in addition to electrodes 15, 16 preferably provided for coagulation of tissue 17, a cutting electrode or the like can be provided. It is also possible to configure the instrument 11 as monopolar instrument (FIG. 7) with only one active electrode 15. A counter electrode 16 is assigned then to the active electrode 15 that is, for example, configured as large area neutral electrode that is to be attached on the patient in order to close the current circuit (FIG. 7).

The instrument 11 is connected with an apparatus 19 via a line, e.g. a two or multiple core cable 18 that is preferably not shielded, that serves for supply of electrical current to the instrument 11.

For further explanation reference is made to FIG. 2. The instrument 11 and the apparatus 19 are schematically illustrated as chain-dashed blocks there. The instrument 11 comprises a radio frequency generator 20 that comprises a radio frequency output 21 and a supply voltage input 22. The radio frequency output is connected to the at least two electrodes 15, 16 in order to supply radio frequency voltage UHF (FIG. 5) to them and to supply a respective radio frequency current. The voltage applied to the electrodes 15, 16 is typically in the range between 100 V and multiple 100 V. It can in individual cases also have remarkably higher values, e.g. up to multiple 1000 V peak voltage, e.g. for supply of cutting electrodes.

The supply voltage input 22 is a direct voltage input or, if a rectifier block G is present, an input for low frequency alternating voltage. In this case the supply voltage input 22 can be configured depending on the used rectifier circuit to accept direct voltage as well as low frequency alternating voltage. The supply voltage input 22 is connected to a measurement device 23 via respective lines that detects at least one physical electrical parameter, e.g. a voltage applied to the supply voltage input 22 and/or the current flowing to the supply voltage input 22 and/or the power supplied to the supply voltage input 22 and/or the oscillation frequency of the radio frequency generator 20. For determination of the oscillation frequency the measurement device 23 can detect and evaluate the radio frequency ripple of the current flowing to the radio frequency generator. The frequency of the ripple depends on the oscillation frequency of the radio frequency generator 20. The measurement device 23 can thus detect one or more of the indicated physical parameters and supply respective measurement values to the apparatus 19 via a signal line 24. The signal line 24 can be part of cable 18 that comprises in addition at least two cores 25, 26 for current supply of instrument 11.

Apparatus 19 comprises a voltage source 27 that can output a supply voltage of typically 100 V, 150 V, 200 V or another voltage in the range between 12 and 500 V. The voltage can be a direct voltage or a respective low frequency alternating voltage. The voltage source supplies the voltage with the required power to the instrument. The power to be provided can thereby range from some few Watt up to multiple 100 W and is typically in the range between 100 W and 300 W. The electrical power is supplied to the instrument 11 thereby via cores 25, 26 of cable 18 as direct current or low frequency power.

In the apparatus 19 a voltage modulation device 28 can be provided that is configured to influence the amount of the supply voltage output from apparatus 19. The voltage modulation device 28 can be part of the voltage source 27 or as symbolically illustrated in FIG. 2, can be configured as separate block. The voltage source 27 can be a battery-operated voltage source 27 or a grid-operated voltage source 27. Preferably it effects a potential separation complying with the standard between the power grid and the supply voltage provided on the instrument side.

The instrument 11 and the apparatus 19 illustrated in FIGS. 1 and 2 operate as follows.

When the instrument 11 is connected with apparatus 19 via cable 18, instrument 11 is ready to use. By means of hand lever 14 the jaws with the electrodes 15, 16 can be moved and can hold tissue 17 between each other. The radio frequency generator 20 can now be activated by means of a switch 29. For example, the switch 29 can be connected to the measurement device 23 for this purpose that thereupon sends a release signal to the apparatus 19 via signal line 24. The release signal can have the effect that the voltage source 27 is activated and/or that the voltage modulation device 28 applies the provided direct or alternating voltage to cores 25, 26 and thus supplies voltage and current to the instrument 11. In the simplest case the voltage modulation device 28 is only a switch. Instead of switch 29, also a foot switch or the like can be provided that activates the apparatus 19 or releases current to the cores 25, 26.

Upon activation of the voltage source 27 the radio frequency generator 20 obtains at its supply voltage input 22 the direct voltage or low frequency alternating voltage. It starts to oscillate with radio frequency and to output the treatment voltage or treatment current at its radio frequency output 21. Therefore, it is produced in direct proximity to the electrodes 15, 16, such that electromagnetic interferences in the environment are not to be expected. This avoids particularly the interference of other devices, e.g. during video endoscopy or during robotics applications.

The measurement device 23 monitors the current supply to the radio frequency generator 20, for example, that is in close relationship to the current output at the radio frequency output 21. If for example a desired dependency between treatment duration and power output between the electrodes 15, 16 shall be adjusted, the voltage modulation device 28 can switch off the current supply of instrument 11 after a desired period. If for example a pulse width modulated RF-signal shall be output at the radio frequency output 21, the direct voltage modulation device 28 can modulate the amount of the direct (or alternating) voltage supplied to the instrument 11, e.g. switching it on and off or between two values, for example 10 V and 150 V alternatingly. Also, the voltage modulation device 28 can create a desired internal resistance of the radio frequency generator 20, i.e. a desired voltage/current characteristic curve, e.g. in that the voltage output to the cores 25, 26 is reduced with increasing current according to a desired function. If the measurement device 23 is a current measurement device and if the signal line 24 transmits the current measurement signal to the voltage modulation device 28, the voltage modulation device 28 can adjust the voltage depending on the measured current in a desired manner, e.g. according to a desired curve. If the radio frequency generator 20 operates with constant effectivity, the desired characteristic, i.e. the desired dependency between the RF output voltage and the RF output current, is adjusted at its radio frequency output 21 in this manner.

Cable 28 guides direct voltage and direct current (or low frequency alternating voltage and alternating current) that can be modulated at most with low frequency of some Hertz or some kHz or some 10 kHz, for example. An interfering radiation or leaking of capacitive leak currents via cable 18 does not occur.

The presented concept can be varied in various respects. A first variation is shown in FIG. 3. The instrument 11 according to FIG. 3 comprises a radio frequency generator 20 and electrodes 15, 16. Apart therefrom, the above description applies accordingly subject to the following deviations:

The measurement device 23 is not located in the instrument 11, but in the apparatus 19. As a result, cable 18 indeed contains cores 25, 26, however a signal line is not necessary. Thus, cable 18 can be a simple two-core non-shielded line. An activation switch is not illustrated in FIG. 3. It can be configured as foot switch and can be directly connected with apparatus 19 in order to release or block the output of direct voltage. It is also possible to attach an activation switch 29 on the instrument 11 and to control apparatus 19 via a signal line by means of an activation switch. It is in addition possible to place an activation switch only as on/off-switch in one or both cores 25, 26 in order to supply or to block the voltage provided by apparatus 19 via cable 18 to or from the supply voltage input 22.

A further modification is shown in FIG. 4. In this embodiment radio frequency generator 20, as well as measurement device 23 and also voltage modulation device 28 are arranged in the instrument 11. The apparatus 19 comprises only the voltage source 27 that is configured to output a non-varying direct voltage (or low frequency alternating voltage). For example, the voltage source 27 can be a usual direct voltage power supply, e.g. a high power USB power supply or a voltage source provided on a surgical table, e.g. a socket for direct voltage. It is also possible to provide an alternating voltage source, having for example an alternating voltage of 50 Hz or 60 Hz, as voltage source and to additionally connect the rectifier block G upstream from the voltage modulation device 28. Apart therefrom, the above description referring to preceding embodiments applies accordingly with regard to the function of the system consisting of instrument 11, cable 18 and apparatus 19.

The structure of the radio frequency generator 20 is basically explained in FIG. 5. The radio frequency generator 20 is configured as push-pull-oscillator having at least four switching transistors T1, T2, T3, T4 in total that are preferably configured as field effect transistors (and/or GaN-transistors) (referably n-channel, enhancement type, i.e. self-blocking). Basically, however, also other transistors can be used in identical circuit arrangement, e.g. in case of inversed voltage polarity, p-channel field effect transistors or also bipolar transistors (npn or pnp), IGBTs or the like.

Transistors T1 and T2 are connected with their source electrodes to a common reference potential 30 (ground). The drain electrodes form a tap Z1 and Z2 respectively. The gates of the two transistors T1 and T2 are connected with the tap of the respective other transistor. The transistors T1 and T2 therefore together form a flip-flop having two transistors T1 and T2 operating in push-pull-mode. On the taps Z1 and Z2 squarewave voltages between zero and a few volt (e.g. 20 V) are applied, wherein transistors T1 and T2 are never concurrently on or never concurrently off.

To the taps Z1 and Z2 current inputs of transistors T3 and T4 are connected that operate as voltage amplifiers in common gate arrangement. The current inputs are realized by their source electrodes. The two gates of transistors T3 and T4 are connected with a non-varying voltage that is provided by means of a constant voltage circuit 31.

The drain electrodes of the two transistors T3 and T4 form an amplifier output that is connected with the parallel resonant circuit 32. It consists of a capacitor 33 (or multiple capacitors arranged, for example, in series connection) and an inductor 34 (or multiple inductors connected in series). The inductor 34 comprises a tap 35 that is connected with the positive potential of the supply voltage input 22.

A decoupling inductor 36 serves for decoupling RF power from the parallel resonant circuit 32, wherein the decoupling inductor 36 is coupled with inductor 34 in transformer coupling manner. Inductor 36 is connected with electrodes 15, 16 without interposition of additional components and thus outputs RF power to them. As necessary, an additional decoupling inductor 36' can be provided that serves for supply of additional electrodes, e.g. a cutting electrode S, that is not illustrated in further detail. For example, it can be located in a jaw of instrument 11. The inductor 36' can be connected in series with inductor 36 in order to output an increased voltage. It is also possible to select a different inductor configuration. Preferably the decoupling inductor forms together with tissue 17 held between electrodes 15, 16 a galvanic circuit without branches.

Transistors T1 and T3 together form a cascode circuit. Likewise transistors T2 and T4 together form a cascode circuit. The parallel resonant circuit 32 forms together with the two cascode circuits a push-pull-oscillator with parallel resonant circuit 32 that defines the oscillating frequency of the push-pull-flip-flop T1, T2. The push-pull-oscillator can be entirely symmetrically or, as it is preferred, also slightly asymmetrically configured with regard to structure and to dimensioning. The asymmetry can exist in component variations, particularly with regard to transistors, in a slight inductor asymmetry (tap of resonant inductor is not exactly centered), in different stray capacitances or the like. This can, for example support the start of oscillation of the radio frequency oscillator.

Figure 6:
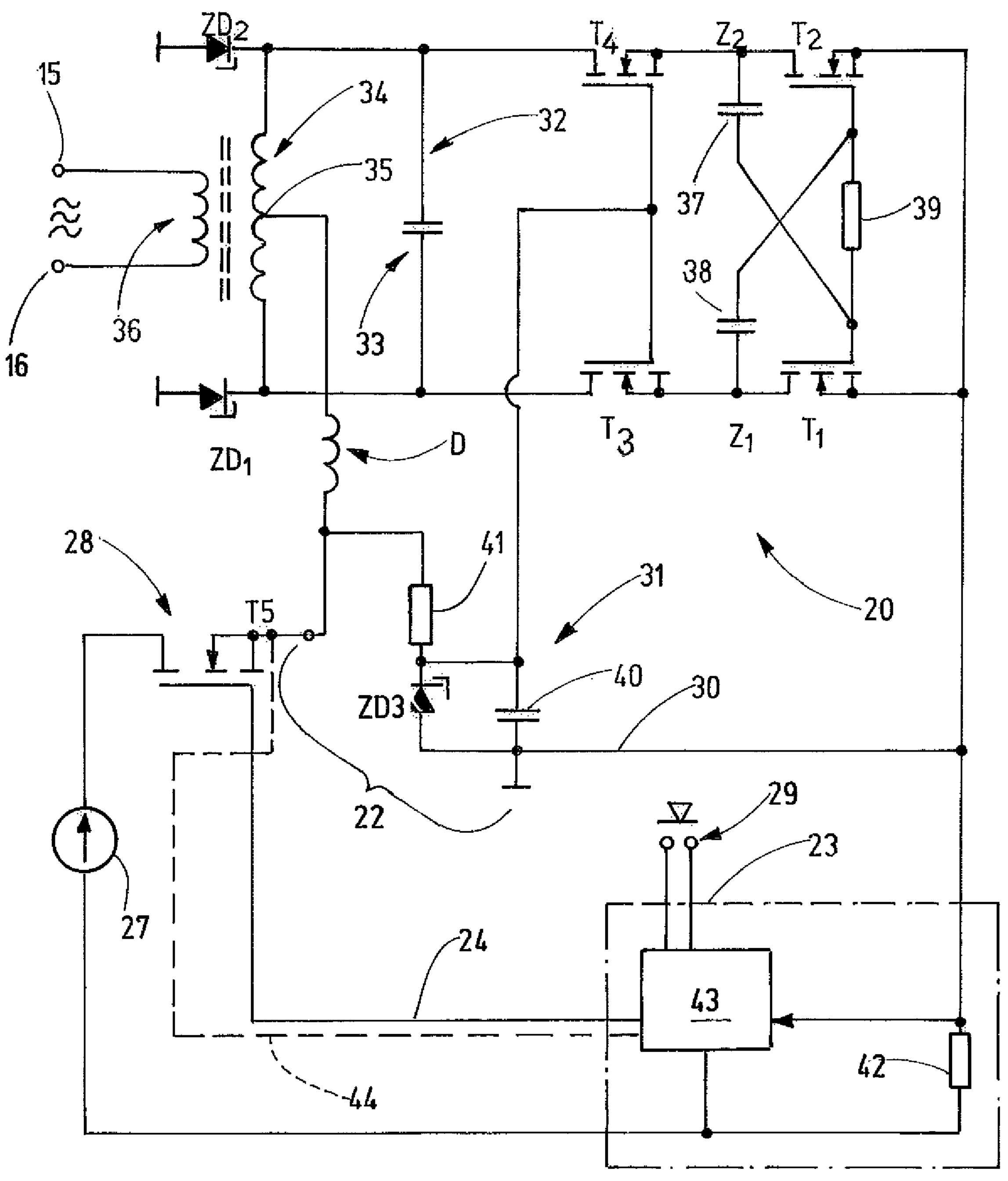

FIG. 6 illustrates the radio frequency generator 20 according to FIG. 5 in a slightly more detailed illustration. Based on the description of the circuit according to FIG. 5 above, it is in addition indicated that the push-pull-flip-flop formed by transistors T1 and T2 can comprise a capacitive coupling in that the taps Z1 and Z2 are connected via capacitors 37, 38 respectively with gates of transistors T1 and T2. In addition, the two gates can be connected with one another via a resistor 39 in order to be kept on the same potential in time average. Preferably, capacitors 37, 38 define together with resistor 39 a flip-flop frequency of the push-pull-flip-flop realized by transistors T1 and T2 that is lower than the oscillating frequency set by parallel resonant circuit. Transistors T1 to T4 can be arranged in a common housing and usually do not require cooling; they are non-cooled.

The parallel resonant circuit can be connected via two Z-diodes ZD1 and ZD2 with reference potential 30 in order to avoid over-voltages at the parallel resonant circuit 32.

The constant voltage circuit 31 can be realized by a parallel connection of Z-diode ZD3 and a capacitor 40 to which current is supplied via a resistor 41.

The circuit according to FIG. 6 comprises in addition to the radio frequency generator 20 also the measurement device 23 that is here by way of example represented by a shunt 42. It is realized by a low ohmic resistor that is located in a line leading from the voltage source 27 to the radio frequency oscillator 20. In addition, a block 43 is part of the measurement device 23 that detects the voltage applied over shunt 42 for current measurement and supplies a respective control signal to the voltage modulation device 28. Via a line 44 block 43 can also detect the voltage applied at a voltage input 22.

The voltage modulation device 28 can be realized by a transistor T5, the drain source connection (or collector emitter connection) of which is arranged in a line leading from the voltage source 27 to the supply voltage input 22. The signal line 24 can be connected with the gate of transistor T5.

For smoothing the current supplied by the voltage source 27 to the radio frequency generator 20 a reactor D can be provided in the line leading to the tap 35. In addition, a buffer capacitor can be provided at the voltage input (downstream the rectifier block G, if it is present).

Block 43 can control the desired function of radio frequency generator 20. As long as radio frequency generator 20 receives a constant voltage via transistor T5, it provides a specific radio frequency voltage for applying current to the electrodes 15, 16 at its output. The current flowing to the electrodes 15, 16 is detected by means of shunt 42 and block 43. The block 43 can define a desired current/voltage dependency. It is possible to provide that different current/voltage dependencies are provided and are selectable. For example, if the generator output voltage shall be reduced with increasing current, block 43 can control transistor T5 via line 24 accordingly. The block 43 can be connected with the supply voltage input 22 via a line that is shown in dashed lines in FIG. 6 and can measure the voltage applied there. The measured voltage can be used for control of transistor T5. Transistor T5 can operate in an analog or in a pulsed (on/off) operation mode. By respective release or blocking of transistor T5 via line 24, radio frequency generator 20 can be switched on or off or can be switched between high power and low power. Other types of modulation are possible.

The concept according to the invention has a variety of advantages. The push-pull-oscillator according to FIGS. 5 and 6 allows a realization in particularly small configuration. No cooling of transistors T1 to T4 is necessary and indeed also not if the radio frequency generator outputs power above 100 W. Moreover, any current or voltage sensor can be omitted in the patient circuit, i.e. on the radio frequency side of the radio frequency generator 20. The patient circuit is a non-branched circuit. The measurement device 23 (as well as additional measurement devices as necessary) can be provided in the direct current circuit. Even the oscillating frequency of the radio frequency generator 20 can be detected at shunt 42, for example, due to the current ripple that occurs there. Current, voltage and power on the primary side indicate the RF voltage on the patient side sufficiently accurately. This is because the losses in the radio frequency generator 20 are low and are substantially constant over its load range. Thus, a closed loop control of the RF voltage, the RF current or the RF power by means of the primary measurement values determined on the direct current side can be realized. Due to omission of the RF-side current and voltage sensors, also the coupling capacitances over the very long isolating distance defined by a standard between the direct current circuit and the RF circuit are reduced. Thus, the radio frequency leak currents of the system are reduced.

For realization of simpler effects, such as a bipolar coagulation, the closed loop control can also be completely omitted. For example, the power curve of the non-closed loop controlled radio frequency generator 20 can be adapted to the surgical application for this purpose. The load impedance (that is resistance of biological tissue 17) then defines the flowing current. Corresponding adjustments can be made by modification of the output circuitry of the generator, e.g. the winding ratio of inductors 34, 36 relative to one another, or by respective definition of the coupling factor between inductors 34, 36. By suitable dimensioning of the coupling factor between the resonant circuit inductor 34 and the decoupling inductor 36 by means of the L/C-ratio of the resonant circuit, by suitable dimensioning of reactor D, the internal resistance of the radio frequency generator can be determined, i.e. the dependency of the RF current from the load formed by tissue 17.

Such an adjustment can also be made by interference at another point, e.g. by modification of the gate bias of gates of transistors T3, T4. In addition, no complex monitoring of specific load conditions is necessary, such as short circuit or idling. Compared with known generators a substantially simplified design results. Also no complex tracking of frequency by means of control is necessary, as it is the case in known generators. The self-oscillating system, i.e. the radio frequency generator 20, neither requires external clock generators nor specific monitoring circuits.

As illustrated in FIG. 7, radio frequency generator 20 can also be arranged on neutral electrode 16 that has therefore to be considered as part of instrument 11. The above description of embodiments according to FIGS. 1-6 applies accordingly on the basis of the already introduced reference signs. In all embodiments the location of the radio frequency generator 20 in instrument 11 or next to the instrument 11 also provides the possibility to reasonably use generators with higher frequencies, e.g. 4 MHz. Even in case of such highly radiating frequencies, the originating interferences and capacitive leak currents are low in the concept according to the invention.

FIG. 8 illustrates an expedient embodiment of the invention having an instrument 11 that is releasably connected with radio frequency generator 20, the latter can be directly configured to be plugged on the housing of the instrument 11, for example, or can be arranged in the extension of cable 18. For example, the radio frequency generator 20 can also be arranged in the proximal connector of cable 18 with which cable 18 is to be connected to apparatus 19. The instrument according to FIG. 8 can be a non-closed loop controlled operating radio frequency generator 20, the internal resistance on the RF output side of which is adapted to the desired surgical effect, e.g. coagulation or tissue fusion. The internal resistance of the radio frequency generator 20 can be linear or non-linear. It can be defined as desired by respective dimensioning of the coupling factor between the inductors 34, 36 (FIGS. 5 and 6), by dimensioning of an appropriate value of reactor D (FIG. 6) or also by a respective setting of internal resistance of voltage source 18. In the embodiment according to FIG. 8, the measurement device 23 and the voltage modulation device 28 can be omitted. It is however also possible to arrange the measurement device 23 and the voltage modulation device 28 either directly on the radio frequency generator 20 or as an alternative in the apparatus 19, as it is the basis of FIG. 3. In all such modifications that are based on the embodiment according to FIG. 8 the generator can be attached in the instrument cable 18 that can be removed from instrument 11 and is thus reusable. Instrument 11 can then be provided only for single use and subsequent disposal. The generator 20 can also be provided in a separate housing as intermediate connector or intermediate cable that is to be attached between instrument 11 and its cable 18 and the apparatus 19. The radio frequency generator 20 can also be provided in a separate removable housing on or in the proximity of neutral electrode 16, as inspired by FIG. 7.

The electrosurgical instrument 11 according to the invention comprises at least one electrode 15, 16 for electrically acting on biological tissue. The electrode is coupled with a radio frequency generator 20 that is arranged in direct proximity of electrode 15 and/or 16. The radio frequency generator oscillates in a self-controlled manner with a frequency between 100 kHz and 10 MHz and is preferably supplied by a constant or timely varying direct voltage. The instrument 11 is thus connected via a line supplying a low frequency voltage or direct voltage with a supplying source, e.g. an apparatus 19.

REFERENCE SIGNS

10 arrangement
11 instrument
12 handle
13 shank
14 hand lever
15 electrode
16 electrode or neutral electrode
17 biological tissue
18 cable
19 apparatus
20 radio frequency generator
21 radio frequency output
22 supply voltage input
G optional rectifier block
UHF radio frequency voltage
23 measurement device
24 signal line
25, 26 cores of cable 18
27 voltage source
28 voltage modulation device
29 switch
30 reference potential
T1-T4 transistors
31 constant voltage circuit
32 parallel resonant circuit
33 capacitor
34 inductor
35 tap
36, 36' decoupling inductor(s)
S cutting electrode
37, 38 capacitors
39 resistor
ZD1-ZD4 Z-diodes
40 capacitor
41 resistor
42 shunt
T5 transistor
D reactor
43 block, measurement device
44 conductor

The invention claimed is:

1. An electrosurgical instrument (11) for treatment of human or animal patients, the electrosurgical instrument comprising:
- at least two electrodes (15, 16) configured to apply current to biological tissue (17);
- at least one radio frequency generator (20) configured as a push-pull-oscillator that comprises a supply voltage input (22) and a radio frequency output (21) connected to the at least two electrodes (15, 16), wherein the radio frequency generator (20) is configured to convert a temporally constant or temporally varying supply voltage into a radio frequency alternating voltage; and
- a line (18) connectable to a voltage source (27) for current supply of the radio frequency generator (20) at its supply voltage input (22);
- wherein the push-pull-oscillator comprises a push-pull flip-flop having two alternatingly switching transistors (T1, T2), the alternatingly switching transistors each comprising an output electrode to which a respective voltage amplifier (T3, T4) is connected.

2. The electrosurgical instrument according to claim 1, wherein the radio frequency generator (20) is configured to provide a voltage (UHF) having a frequency in a range of 100 kHz to 10 MHz.

3. The electrosurgical instrument according to claim 1, wherein each of the voltage amplifiers (T3, T4) is connected to the output electrode of the respective alternatingly switching transistor (T1, T2) in common gate or common base circuit.

4. The electrosurgical instrument according to claim 1, wherein the radio frequency generator (20) comprises a parallel resonant circuit (32) comprising at least one inductor (34) and at least one capacitor (33) that are connected in parallel to one another and a decoupling circuit that is exclusively connected to the at least two electrodes (15, 16) for electrically acting on the biological tissue (17).

5. The electrosurgical instrument according to claim 4, wherein the at least one inductor (34) of the radio frequency generator (20) is in transformer coupling arrangement with a decoupling inductor (36, 36') and the decoupling inductor (36, 36') is connected with the at least two electrodes (15, 16).

6. The electrosurgical instrument according to claim 1, wherein the radio frequency generator (20) is releasably connected with the electrosurgical instrument (11).

7. The electrosurgical instrument according to claim 1, wherein the radio frequency generator (20) is a non-closed loop controlled radio frequency generator that comprises a current/voltage characteristic that is adapted to a surgical application.

8. The electrosurgical instrument according to claim 1, wherein the supply voltage input (22) is connected to at least one measurement device (23).

9. The electrosurgical instrument according to claim 8, wherein the at least one measurement device (23) comprises a current measurement device (42) and/or a voltage measurement device (42) and/or a power measurement device (43) and/or a frequency measurement device (42, 43).

10. An arrangement comprising the electrosurgical instrument (11) according to claim 8, and an apparatus (19) comprising a controllable voltage source (27) to which the electrosurgical instrument (11) is adapted to be connected by a cable (18), wherein the controllable voltage source (27) is configured to be connected to the at least one measurement device.

11. The electrosurgical instrument according to claim 1, wherein the supply voltage input (22) of the radio frequency generator (20) is connected to a voltage modulation device (28).

12. The electrosurgical instrument according to claim 11, wherein the voltage modulation device (28) is connected to at least one measurement device (23), wherein the at least one measurement device (23) comprises a current measurement device (42) and/or a voltage measurement device (42) and/or a power measurement device (43) and/or a frequency measurement device (42, 43).

13. An arrangement comprising the electrosurgical instrument according to claim 1, and an apparatus (19) having a voltage source (27) adapted to be connected to the electrosurgical instrument (11) by a cable (18).

14. The arrangement according to claim 13, wherein at least one measurement device (23) is arranged in the apparatus (19) having the voltage source (27).

15. The arrangement according to claim 14, wherein the at least one measurement device (23) comprises a current measurement device (42) and/or a voltage measurement device (42) and/or a power measurement device (43) and/or a frequency measurement device (42, 43).

* * * * *